United States Patent
Kurosawa et al.

(10) Patent No.: US 7,330,265 B2
(45) Date of Patent: Feb. 12, 2008

(54) APPEARANCE INSPECTION APPARATUS AND PROJECTION METHOD FOR PROJECTING IMAGE OF SAMPLE UNDER INSPECTION

(75) Inventors: Toshiro Kurosawa, Hachioji (JP); Shohei Yamazaki, Hachioji (JP); Yoko Miyazaki, Hachioji (JP)

(73) Assignee: Tokyo Seimitsu Co., Ltd., Tokyo (JP)

( * ) Notice: Subject to any disclaimer, the term of this patent is extended or adjusted under 35 U.S.C. 154(b) by 0 days.

(21) Appl. No.: 11/177,070

(22) Filed: Jul. 8, 2005

(65) Prior Publication Data

US 2006/0007436 A1    Jan. 12, 2006

(30) Foreign Application Priority Data

Jul. 9, 2004    (JP) .............................. 2004-202900

(51) Int. Cl.
 *G01N 21/55*    (2006.01)
(52) U.S. Cl. ................. 356/445; 356/237.2; 356/237.3
(58) Field of Classification Search .................... None
 See application file for complete search history.

(56) References Cited

U.S. PATENT DOCUMENTS

| | | | | |
|---|---|---|---|---|
| 5,587,832 | A * | 12/1996 | Krause | 359/385 |
| 6,104,945 | A * | 8/2000 | Modell et al. | 356/317 |
| 6,392,748 | B1 * | 5/2002 | Fateley | 356/330 |
| 6,686,602 | B2 * | 2/2004 | Some | 356/237.1 |
| 6,867,424 | B2 | 3/2005 | Kurosawa et al. | |
| 6,979,830 | B2 * | 12/2005 | Dietz et al. | 356/417 |
| 7,094,506 | B2 * | 8/2006 | Van Buel | 430/5 |
| 7,248,352 | B2 * | 7/2007 | Hamamatsu et al. | 356/237.2 |

FOREIGN PATENT DOCUMENTS

| | | |
|---|---|---|
| JP | 2002-6224 | 1/2002 |
| JP | 2003-149169 | 5/2003 |
| JP | 2004-101403 | 4/2004 |
| JP | 2004-101406 | 4/2004 |

OTHER PUBLICATIONS

Patent Abstract of Japan, Publication No. 2002006224 A, Published on Jan. 9, 2002, in the name of Nonoda.
Patent Abstract of Japan, Publication No. 2003149169 A, Published on May 21, 2003, in the name of Kurosawa, et al.
Patent Abstract of Japan, Publication No. 2004101403 A, Published on Apr. 2, 2004, in the name of Katsuki, et al.
Patent Abstract of Japan, Publication No. 2004101406 A, Published on Apr. 2, 2004, in the name of Katsuki.

* cited by examiner

*Primary Examiner*—Gregory J. Toatley, Jr.
*Assistant Examiner*—Juan D. Valentin, II
(74) *Attorney, Agent, or Firm*—Christie, Parker & Hale, LLP (57) ABSTRACT

An object of the present invention is to provide an appearance inspection apparatus that can change the method of illumination, the shape of illumination light, and a spatial filter for the projection of an image of a sample dynamically during inspection, and also to provide a projection method for projecting the image of the sample. Illumination optics 12 and 13 and imaging optics 21 and 22 in the appearance inspection apparatus are respectively configured to form reflecting optical systems with mirror array devices 16 and 26 disposed at points conjugate to the pupil position 8 of an objective lens 3. The mirror array devices 16 and 26 are controlled in accordance with the field-of-view position of the objective lens 3 on the sample.

6 Claims, 8 Drawing Sheets

APPEARANCE INSPECTION APPARATUS AND PROJECTION METHOD FOR PROJECTING IMAGE OF SAMPLE UNDER INSPECTION

CROSS-REFERENCE TO RELATED APPLICATION

This application claims priority of Japanese Patent Application No. 2004-202900, filed on Jul. 9, 2004.

BACKGROUND OF THE INVENTION

1. Field of the Invention

The present invention relates to an appearance inspection apparatus which captures an image of a pattern formed on a sample such as a wafer, and which detects a defect by processing the captured image signal and, more particularly, to the configuration of the illumination optics and imaging optics used therein.

2. Description of the Related Art

In the fabrication of semiconductor wafers, semiconductor memory photomasks, liquid crystal panels, and the like, repetitive patterns are formed by repeating a prescribed pattern. It is therefore practiced to detect a pattern defect by capturing an optical image of such patterns and by comparing adjacent patterns with each other. As a result of the comparison, if there is no difference between the two patterns, it is determined that the patterns are free from defects, but if there is a difference between them, it is determined that there is a defect in one of the patterns. The following description will be given by taking as an example a semiconductor wafer appearance inspection apparatus which inspects defects in the patterns formed on a semiconductor wafer. However, the present invention is not limited to this particular application, but can also be applied to an appearance inspection apparatus for inspecting defects on a semiconductor memory photomask, a liquid crystal display panel, or the like.

Figure 1:
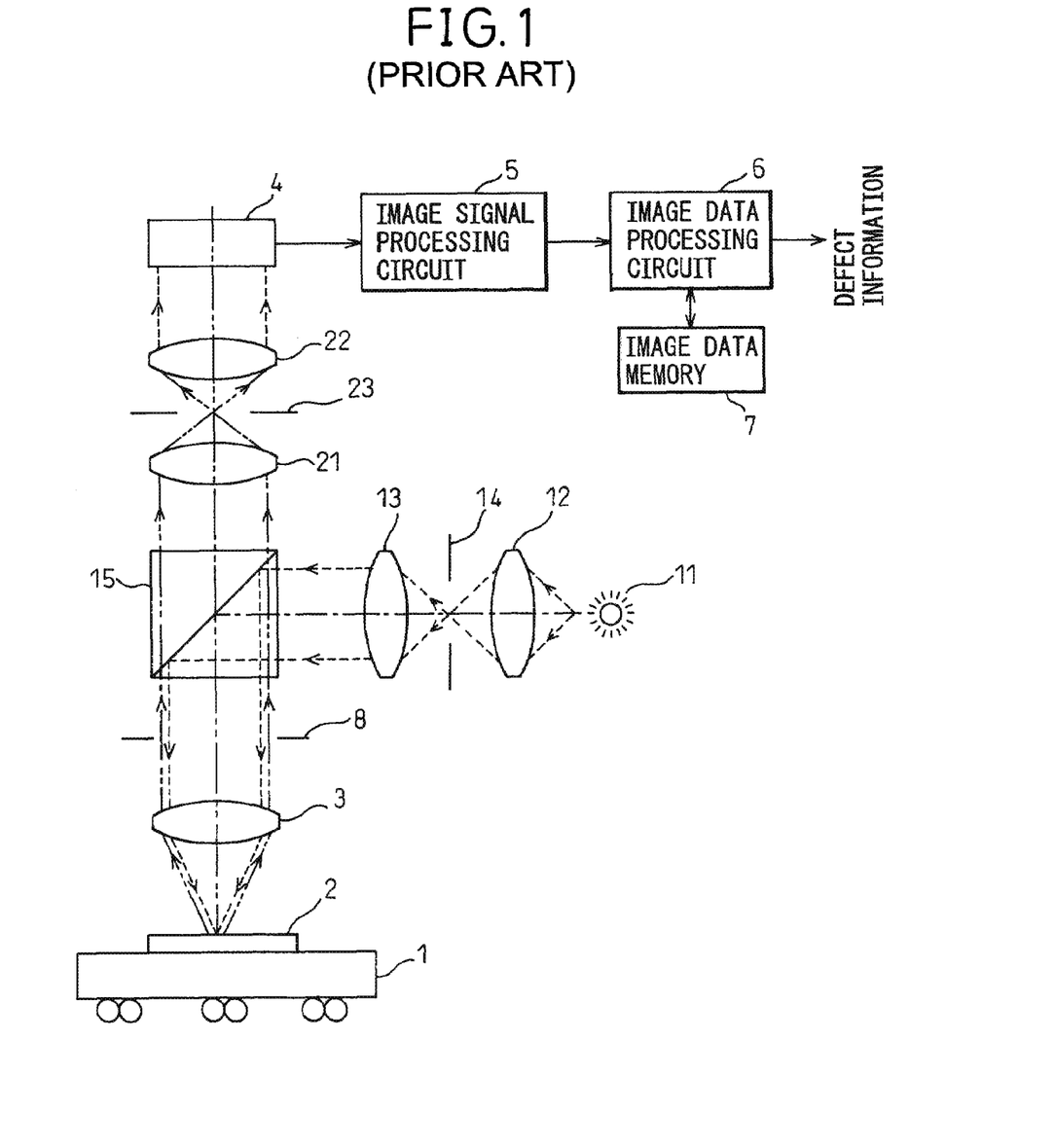
FIG. 1 is a diagram schematically showing the configuration of a semiconductor wafer defect inspection apparatus according to the prior art.

FIG. 1 is a diagram schematically showing the configuration of the semiconductor wafer appearance inspection apparatus. As shown in FIG. 1, the semiconductor wafer appearance inspection apparatus comprises: a stage 1 for holding a semiconductor wafer 2 thereon; an objective lens 3 for projecting an optical image of the surface of the semiconductor wafer 2; an imaging device (image sensor) 4 for converting the projected optical image of the surface of the semiconductor wafer 2 into an electrical image signal; lenses 21 and 22 for projecting the image of the semiconductor wafer 2, projected through the objective lens 3, onto the image sensor 4; an image signal processing circuit 5 for processing the analog image signal output from the image sensor 4 and converting it into multi-valued digital image data; a digital image data processing circuit 6 for processing the digital image data and detecting a defect by comparing corresponding portions between patterns; and an image data memory 7 for storing the image data for the data processing. An illumination optical system for illuminating the surface of the semiconductor wafer 2 comprises a light source 11 and a half mirror (beam splitter) 15 which is placed in the projection light path between the objective lens 3 and illumination lenses 12 and 13.

A TV camera or the like that uses a two-dimensional CCD device may be used as the imaging device 4, but a line sensor such as a one-dimensional CCD is often used in order to obtain a high-definition image signal; in that case, the stage 1 is moved (by scanning) relative to the semiconductor wafer 2, and the image signal processing circuit 5 acquires the image by capturing the signal of the line sensor 4 in synchronism with the drive pulse signal applied to drive the stage 1.

Figure 2A:
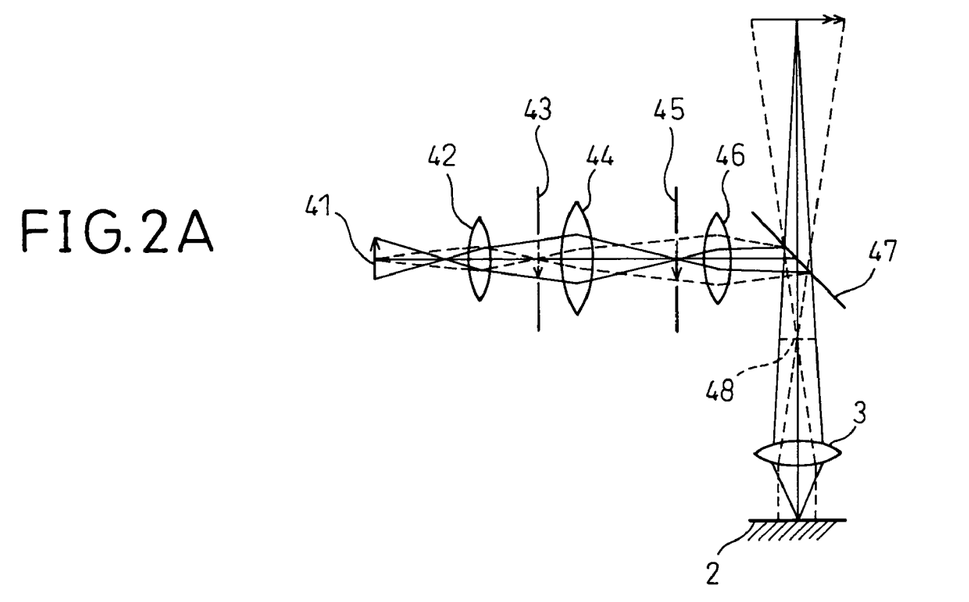
FIG. 2A is a diagram schematically showing the configuration of a bright-field illumination system.
Figure 2B:
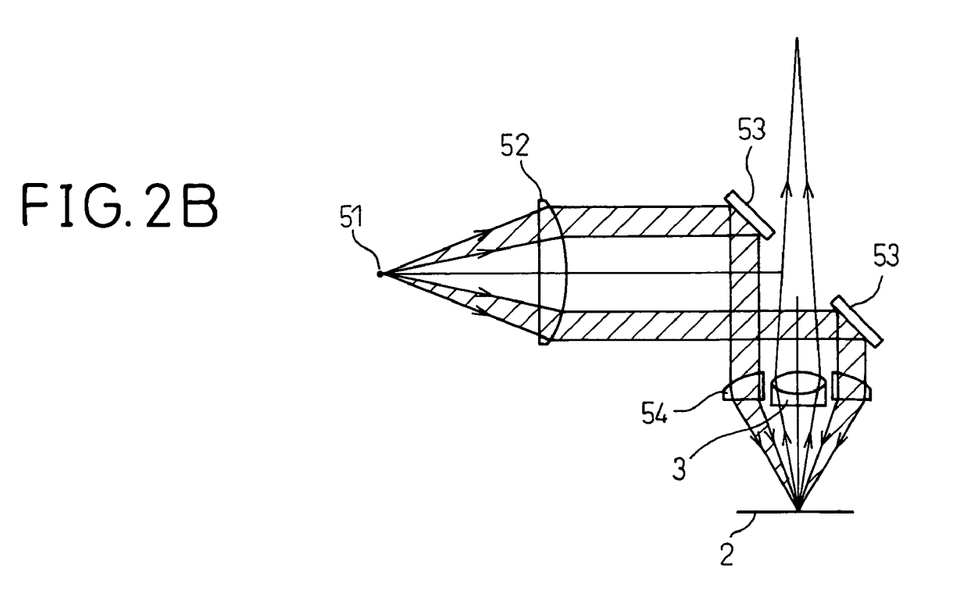
FIG. 2B is a diagram schematically showing the configuration of a dark-field illumination system.

The illumination optical system used in the semiconductor wafer appearance inspection apparatus will be described below. An illumination optical system for a metallographic microscope is used in the semiconductor wafer appearance inspection apparatus. For the illumination optical system of the metallographic microscope, a bright-field illumination system such as shown in FIG. 2A and a dark-field illumination system such as shown in FIG. 2B are known. In the bright-field illumination system, illumination light from a light source 41 is directed through a lens 42, an aperture stop 43, a lens 44, a field stop 45, and a lens 46 to a half mirror 47 provided in the projection path; then, the light is reflected by the half mirror 47 toward the objective lens 3, and the light passed through the objective lens 3 illuminates the surface of the sample (wafer) 2. The lens 42 projects the image of the light source 41 to the position of the aperture stop 43, and the lenses 44 and 46 project that image to the position indicated by reference numeral 48. This position is the pupil position of the objective lens 3; the illumination light projected to this point illuminates the surface of the wafer 2 with uniform light free from unevenness in light distribution. In the bright-field illumination system, the surface of the wafer 2 is illuminated from the perpendicular direction containing the optical axis of the objective lens, and an image of its specularly reflected light is captured.

On the other hand, in the dark-field illumination system, illumination light from a light source 51 is converted into an annular beam of light by blocking its center portion, as shown in FIG. 2B, and the annular beam of light is then converted into a substantially parallel beam of light through a lens 52. This annular parallel beam of light is projected onto a ring mirror 53 which reflects the beam of light in a direction parallel to the optical axis of the objective lens 3. The ring mirror 53 is a ring-shaped (or more specifically, ellipsoidal ring-shaped) reflective mirror which allows light to pass through its center portion centered around the optical axis of the objective lens 3 but reflects light at its outer peripheral portion. The annular illumination light reflected by the ring mirror 53 is focused through a ring-shaped condenser lens 54 and illuminates the portion of the wafer 2 near the optical axis of the objective lens 3.

As illumination light specularly reflected at the surface of the wafer 2 is not captured, the dark-field illumination system has the advantage of increasing the relative signal strength of the diffracted light occurring due to the presence of a defect (a short circuit) on the wafer 2; in recent years, the need to inspect the patterns on wafers under dark-field illumination has been rapidly increasing because of ever decreasing pattern feature size.

As described above, the bright-field illumination system and the dark-field illumination system have their own advantages, and appearance inspection apparatuses have been designed that have both the bright-field illumination system and the dark-field illumination system and that are capable of switching between these two systems.

For example, Japanese Unexamined Patent Publication No. 2003-149169 discloses an appearance inspection apparatus comprising a bright-field illumination system for providing illumination light that covers the range containing the optical axis of the objective lens, and a dark-field illumination system for providing illumination light that covers a range outside the region centered around the optical axis of the objective lens by using a reflective mirror mounted in a position outside the projection path of the objective lens.

On the other hand, Japanese Unexamined Patent Publication No. 2004-101406 discloses an appearance inspection apparatus that achieves both bright-field illumination and dark-field illumination by providing circular filters complementary to each other, one disposed at a conjugate point 14 to the pupil plane 8 of the objective lens provided in the illumination optical system implementing the bright-field illumination system and the other at a conjugate point 23 to the pupil plane 8 of the objective lens provided in the imaging optical system.

Likewise, Japanese Unexamined Patent Publication No. 2004-101403 discloses an appearance inspection apparatus that comprises a circular filter provided at a conjugate point 14 to the pupil plane 8 of the objective lens provided in the illumination optical system implementing the bright-field illumination system, a polarization mirror as a beam splitter 15, and a member containing a half-wave plate provided between the objective lens 3 and the polarization mirror, and that achieves an effect equivalent to that of a dark-field illumination system by blocking low-order diffracted light from the sample under inspection.

Next, the projection optical system (imaging optical system) used in the appearance inspection apparatus will be described. In the appearance inspection apparatus, the lenses 21 and 22 are arranged as imaging optics for projecting the image of the sample 2, projected through the objective lens 3, at a desired magnification onto the image sensor 4. Here, an image of the frequency component intensity distribution of the image of the sample 2 under observation is formed in the pupil plane 8 of the objective lens 3; accordingly, by providing a spatial filter (spatial frequency filter) at the pupil plane 8 or at the conjugate point 23 to the pupil plane 8 in the imaging optical system, when the image under observation is an image of a pattern having periodicity such as a pattern in a memory cell area, for example, the frequency components corresponding to the pattern can be masked and the relative signal strength of diffracted light occurring from other portions, i.e., defective (short circuited) portions, can be increased.

For example, U.S. Pat. No. 6,686,602 discloses an appearance inspection apparatus in which a programmable spatial filter is provided at the Fourier plane of the objective lens 3.

SUMMARY OF THE INVENTION

Since patterns of various geometries are formed on the dies fabricated on a semiconductor wafer, it is desirable that the method of illumination for appearance inspection be changed in accordance with the pattern formed in the portion under inspection.

For example, when the pattern has a particular orientation, it is desirable to provide illumination in accordance with the orientation of the pattern, instead of providing omnidirectional illumination. In particular, in an area where parallel line patterns are formed, diffracted light occurring from a defect between lines becomes easier to detect if the illumination light is projected that has an azimuth angle along the direction of the parallel lines.

However, in the prior art appearance inspection apparatus, it has not been possible to change the method of illumination or the shape of the illumination light in accordance with the pattern on the sample portion under inspection, because the apparatus is designed to provide omnidirectional illumination as shown in the above-cited patent documents. Further, it has not been possible to change the illumination shape dynamically during the inspection.

Further, when the observation area is in a periodic pattern area such as a memory cell area, it would be preferable to arrange spatial filters at the conjugate points 14 and 23 to the pupil plane 8 of the objective lens, as earlier described, and to perform the observation under dark-field illumination so as to increase the relative signal strength of the diffracted light occurring from a defect, but when the observation area has moved into a logic circuit area or other peripheral circuit area (peripheral area), it would be preferable to perform the observation under bright-field illumination.

It is therefore preferable to dynamically change the method of illumination and the shape of the filter disposed at the pupil plane 8 or its conjugate point 23 in accordance with the patterned area located in the region under observation but, in the prior art appearance inspection apparatus, it has not been possible to change the method of illumination or the spatial filter for the projection of the image of the sample dynamically during the observation.

Accordingly, it is an object of the present invention to provide an appearance inspection apparatus that can change the method of illumination, the shape of illumination light, and the spatial filter for the projection of the image of the sample dynamically during inspection, and also to provide a projection method for projecting the image of the sample.

To achieve the above object, in an appearance inspection apparatus according to the present invention, illumination optics and imaging optics are respectively configured as reflecting optical systems with mirror array devices disposed at points conjugate to the pupil position of an objective lens, and the mirror array devices are controlled in accordance with the field-of-view position of the objective lens on the sample.

More specifically, according to a first aspect of the present invention, there is provided an appearance inspection apparatus comprising: a light source; an objective lens; an illumination optical system for projecting illumination light from the light source onto a sample through the objective lens; and an imaging optical system for projecting an image of the sample, projected through the objective lens, onto an imaging device, wherein the illumination optical system is configured as a reflecting optical system with a mirror array device disposed at a point conjugate to the pupil position of the objective lens.

The imaging optical system may also be configured as a reflecting optical system with a mirror array device disposed at a point conjugate to the pupil position of the objective lens, and the appearance inspection apparatus may further include a mirror controller for controlling the mirror array devices in the illumination optical system and the imaging optical system in accordance with the field-of-view position of the objective lens on the sample.

According to a second aspect of the present invention, there is provided a method of image projection for use in the appearance inspection apparatus, the method being characterized in that the illumination optical system is configured as a reflecting optical system with a mirror array device disposed at a point conjugate to the pupil position of the objective lens, and in that the illumination light from the light source is filtered through the mirror array device.

Here, the imaging optical system may also be configured as a reflecting optical system with a mirror array device disposed at a point conjugate to the pupil position of the objective lens so that the image of the sample projected through the objective lens may be filtered through the mirror array device; further, the mirror array devices respectively arranged in the illumination optical system and the imaging optical system may be controlled in accordance with the field-of-view position of the objective lens on the sample.

BRIEF DESCRIPTION OF THE DRAWINGS

These and other objects and features of the present invention will become clearer from the following description of the preferred embodiments given with reference to the attached drawings, wherein:

FIG. 5, including FIGS. 5A and 5B, is a diagram showing a top plan view and an enlarged view of a first example of a semiconductor wafer as a sample under inspection;

FIG. 7, including FIGS. 7A and 7B, is a diagram showing a top plan view and an enlarged view of a second example of a semiconductor wafer as a sample under inspection;

DESCRIPTION OF THE PREFERRED EMBODIMENTS

Preferred embodiments of the present invention will be described in detail below while referring to the attached drawings.

Figure 3:
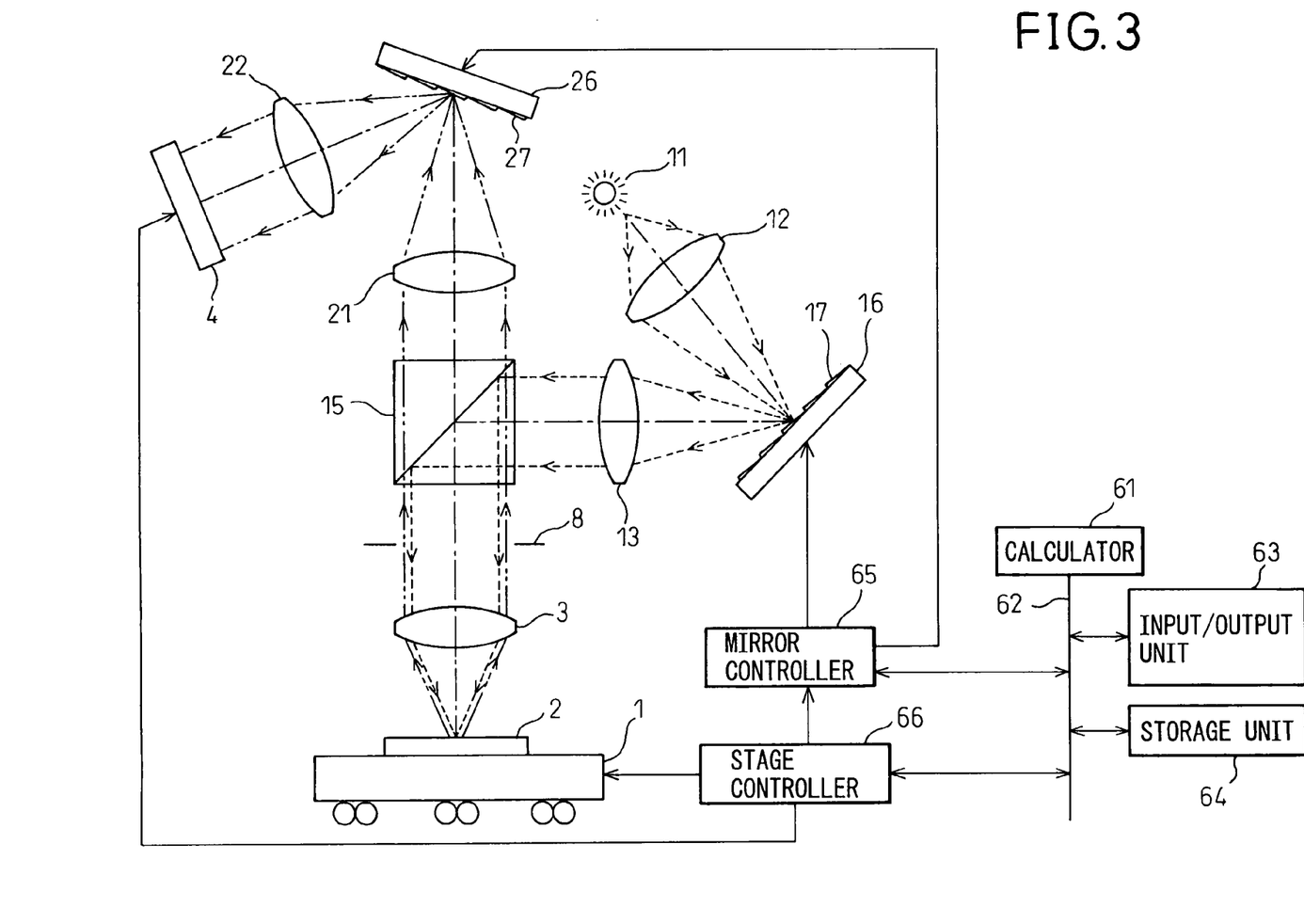
FIG. 3 is a diagram showing portions relating to the optics used in a semiconductor wafer appearance inspection apparatus according to an embodiment of the present invention.

FIG. 3 is a diagram showing portions relating to the optics used in a semiconductor wafer appearance inspection apparatus according to an embodiment of the present invention. Other portions shown in FIG. 1 are omitted here. The following description will be given by taking as an example the semiconductor wafer appearance inspection apparatus which inspects defects in the patterns formed on a semiconductor wafer; however, the present invention is not limited to this particular application, but can also be applied widely to appearance inspection apparatuses for inspecting semiconductor memory photomasks and semiconductor devices such as liquid crystal display panels.

As shown in FIG. 3, the semiconductor wafer defect inspection apparatus of the present embodiment comprises: a stage 1 for holding a semiconductor wafer 2 thereon; an objective lens 3 for projecting an optical image of the surface of the semiconductor wafer 2; an image sensor 4 for converting the projected optical image of the surface of the semiconductor wafer 2 into an electrical image signal; a half mirror (beam splitter) 15 disposed in the projection light path of the objective lens 3; a light source 11; an illumination optical system; and an imaging optical system.

For the image sensor 4, it is preferable to use a one-dimensional line sensor such as TDI. In that case, the stage 1 is moved (by scanning) relative to the semiconductor wafer 2, and the image signal processing circuit 5 acquires the image by capturing the signal of the line sensor 4 in synchronism with the drive pulse signal applied from a stage controller 66 to drive the stage 1. Alternatively, a TV camera or the like that uses a two-dimensional CCD device may be used.

The illumination optical system is one for projecting illumination light from a light source 11 onto the semiconductor wafer 2 through the objective lens 3, and is constructed from a reflecting optical system comprising illumination lenses 12 and 13, which gather the light radiated from the light source 11, and a mirror array device 16, which is placed at a conjugate point occurring between the illumination lenses 12 and 13 with respect to the position (pupil position) of the pupil plane 8 of the objective lens 3, and which reflects the illumination light focused through the lens 12 and directs it into the lens 13.

The imaging optical system is one for projecting the image of the semiconductor wafer 2, projected through the objective lens 3, onto the image sensor 4, and is constructed from a reflecting optical system comprising a projection lens 21, 22, which projects the projected image from the objective lens 3 onto the image sensor 4, and a mirror array device 26, which is placed at a conjugate point occurring between the lenses 21 and 22 with respect to the position of the pupil plane 8 of the objective lens 3, and which reflects the projected image focused through the lens 21 and directs it into the lens 22.

The surface of each of the mirror array devices 16 and 26 is covered with a large number of very small mirrors or micromirrors 17, 27, and the angle of the reflecting surface of each individual micromirror 17, 27 is controllable. Digital Micromirror Devices (DMDS)™ developed by Texas Instruments can be used for the mirror array devices 16 and 26.

In the pupil plane 8 of the objective lens 3, there occurs an image of the same shape as the image of the illumination light focused on the mirror array device 16 placed at a point conjugate to the pupil plane 8 of the objective lens 3. Accordingly, if, of the micromirrors 17 contained in the mirror array device 16, only the micromirrors 17 corresponding to the illuminating portion of the illumination light image focused at the pupil plane 8 are controlled so as to orient in a direction in which these micromirrors 17 reflect the light toward the lens 13, and the other micromirrors 17 are controlled so as to orient in a direction in which these other micromirrors 17 do not reflect the light toward the lens 13, then the shape of the illuminating portion of the illumination light image focused at the pupil plane 8 can be changed as desired.

Likewise, on the mirror array device 26 in the imaging optical system, there occurs an image of the same shape as the projected image of the semiconductor wafer 2 focused at the pupil plane 8 of the objective lens 3. Accordingly, if, of the micromirrors 27 contained in the mirror array device 26, only the micromirrors 27 corresponding to the portion of the projected image that needs to be projected onto the image sensor 4 are controlled so as to orient in a direction in which these micromirrors 27 reflect the light toward the lens 22, and the other micromirrors 27 are controlled so as to orient in a direction in which these other micromirrors 27 do not reflect the light toward the lens 22, then a spatial filter for filtering the projected image of the semiconductor wafer 2 can be formed at the conjugate point to the pupil plane 8 of the objective lens 3.

Figure 4A:
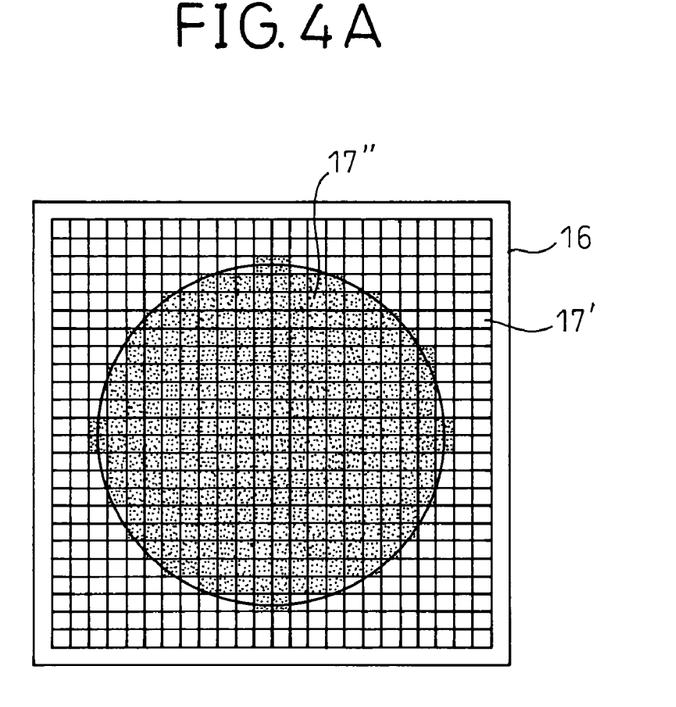
FIG. 4A is a diagram for explaining how individual mirrors are controlled on a mirror array device in an illumination optical system when providing dark-field illumination.
Figure 4B:
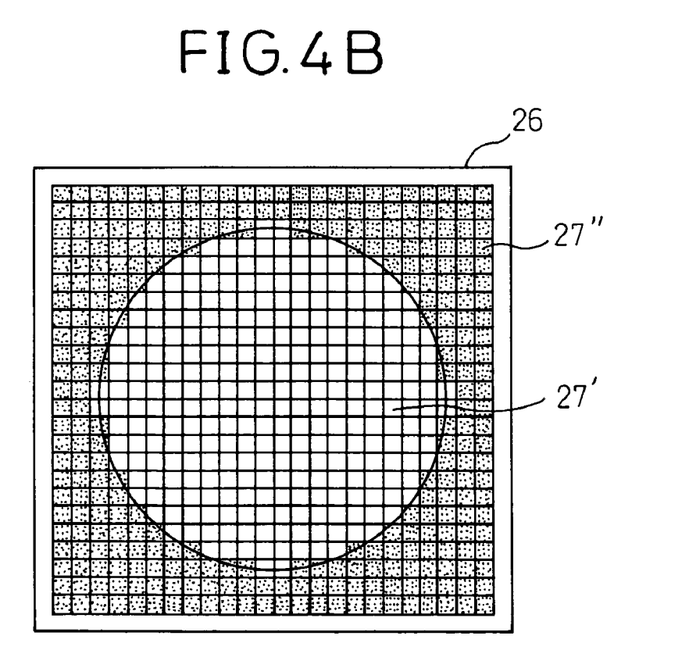
FIG. 4B is a diagram for explaining how individual micromirrors are controlled on a mirror array device in an imaging optical system when providing dark-field illumination.

FIG. 4A shows how the individual micromirrors 17 are controlled on the mirror array device 16 in the illumination optical system when providing dark-field illumination by the light source 11, and FIG. 4B shows how the individual micromirrors 27 are controlled on the mirror array device 26 in the imaging optical system when providing dark-field illumination by the light source 11. In FIG. 4A, the mirrors 17" positioned in the hatched area are the micromirrors whose orientation is controlled so as not to reflect the light toward the lens 13, and the other mirrors 17' outside the hatched area are the micromirrors whose orientation is controlled so as to reflect the light toward the lens 13. Likewise, in FIG. 4B, the mirrors 27" positioned in the hatched area are the micromirrors whose orientation is controlled so as not to reflect the light toward the lens 22, and the other mirrors 27' positioned in the area enclosed by the hatched area are the micromirrors whose orientation is controlled so as to reflect the light toward the lens 22. As shown, the patterns shown in FIGS. 4A and 4B are complementary to each other.

The illumination light reflected by the mirror array device 16 controlled as shown in FIG. 4A is focused at the pupil plane 8 of the objective lens 3 as a doughnut-shaped illumination image with a dark region centered around the optical axis of the objective lens 3. Accordingly, the resulting illumination light passes through the peripheral portion of the objective lens 3 and is incident obliquely on the semiconductor wafer 2.

Then, directly reflected light reflecting at the same angle as the incident illumination light and diffracted light reflecting at angles different from the angle of the incident illumination light occur at the surface of the semiconductor wafer 2 illuminated with the light incident obliquely from the peripheral portion of the objective lens 3. Both the directly reflected light and the diffracted light enter the objective lens 3 but, at the pupil plane 8 of the objective lens 3, the directly reflected light is focused only in the peripheral portion, i.e., the portion excluding the portion near the optical axis of the objective lens 3, while the diffracted light is also focused in the portion near the optical axis of the objective lens 3.

Accordingly, when the mirror array device 26 is controlled, as shown in FIG. 4B, so as to form a spatial filter that blocks the projected light in the peripheral portion, i.e., the portion excluding the portion near the optical axis of the objective lens 3, and allows only the projected light near the optical axis to pass through, only the diffracted light occurring from the semiconductor wafer 2 can be projected onto the image sensor 4, thus achieving a dark-field illumination system.

On the other hand, a bright-field illumination system can be achieved by controlling all the micromirrors 17 on the mirror array device 16 in the illumination optical system so as to reflect the light toward the lens 13, thus making the mirror array device 16 simply work as a plane mirror, and by also controlling all the micromirrors 27 on the mirror array device 26 in the imaging optical system so as to reflect the light toward the lens 22, thus making the mirror array device 26 simply work as a plane mirror. Here, it is also possible to adjust the brightness of the bright-field illumination by varying, in the mirror array device 16 of the illumination optical system, the ratio between the micromirrors 17', whose orientation is controlled so as to reflect the light toward the lens 13, and the micromirrors 17", whose orientation is controlled so as not to reflect the light toward the lens 13.

In one example, the ratio between the micromirrors 17', whose orientation is controlled so as to reflect the light toward the lens 13, and the micromirrors 17", whose orientation is controlled so as not to reflect the light toward the lens 13, may be varied by controlling the orientation of the micromirrors 17 in the center portion of the reflecting surface of the mirror array device 16 so as not to reflect the light toward the lens 13 as shown in FIG. 4A, and thereby reducing the proportion of the micromirrors 17 whose orientation is controlled so as to reflect the light toward the lens 13, only in the peripheral portion of the reflecting surface of the mirror array device 16.

Conversely, the proportion of the micromirrors 17, whose orientation is controlled so as to reflect the light toward the lens 13, may be reduced only in the center portion of the reflecting surface of the mirror array device 16 by controlling the orientation of the micromirrors 17 in the peripheral portion of the reflecting surface of the mirror array device 16 so as not to reflect the light toward the lens 13.

Alternatively, the proportion of the micromirrors 17, whose orientation is controlled so as to reflect the light toward the lens 13, may be reduced by selecting micromirrors 17 at prescribed intervals (that is, one micromirror for every prescribed number of micromirrors 17) from among the micromirrors arranged on the mirror array device 16, and by controlling the orientation of the plurality of selected micromirrors 17 so as not to reflect the light toward the lens 13.

In this way, the semiconductor wafer defect inspection apparatus of the present embodiment can be switched between the bright-field illumination system and the dark-field illumination system.

As described above, in the mirror array device 16, the reflecting surface of each individual micromirror 17 is controllable. Furthermore, each individual micromirror can be controlled at high speed (in the order of milliseconds); therefore, while the surface of the semiconductor wafer 2 is being scanned with the objective lens 3 for inspection, the shape of the illumination light can be changed dynamically in accordance with each pattern that sequentially comes into the field of view for inspection.

Figure 5:
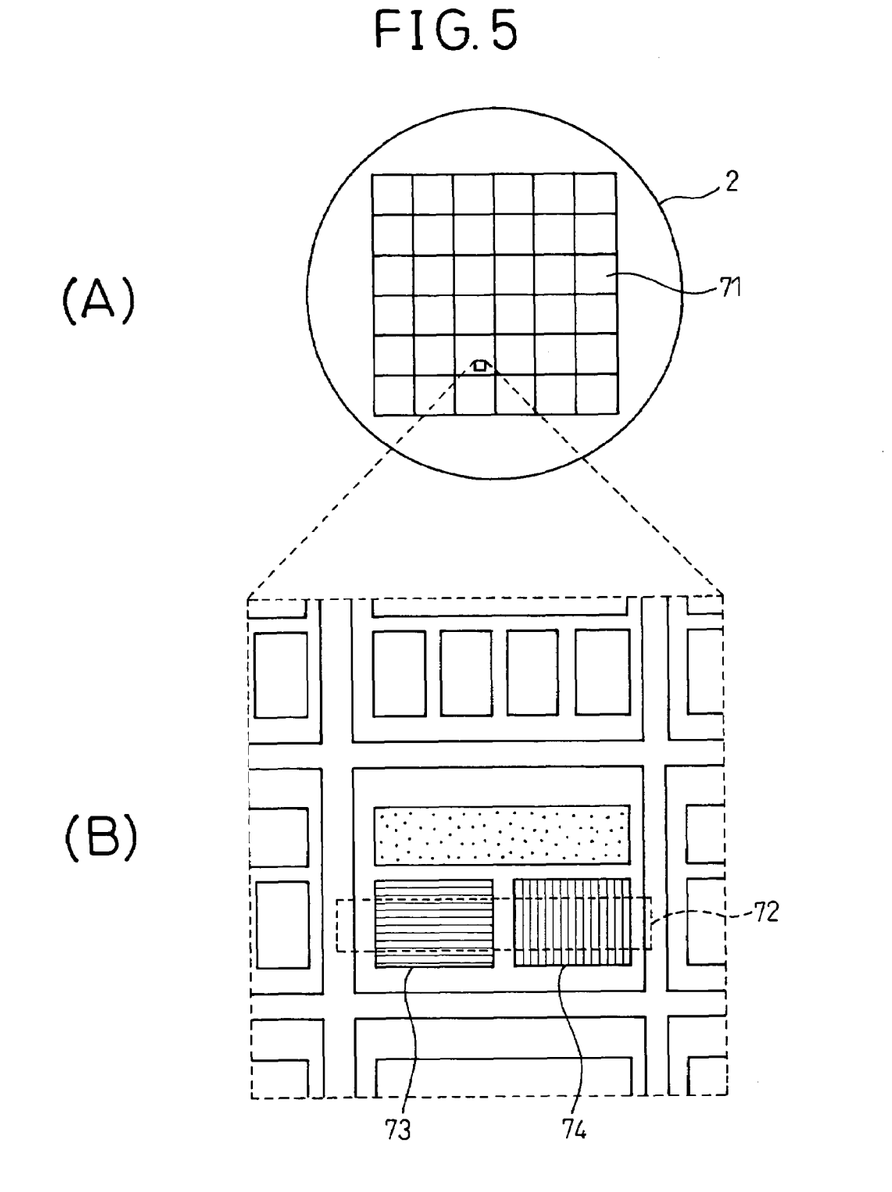

For example, a case where a plurality of dies 71 on which circuit patterns are formed are fabricated on the semiconductor wafer 2 as shown in part (A) of FIG. 5, and pattern areas having various orientations are formed on each die 71 as shown in part (B) of FIG. 5, and where the azimuth angle of the illumination light is changed while scanning the field of view of the objective lens 3 within an area 72 may occur.

Figure 6A:
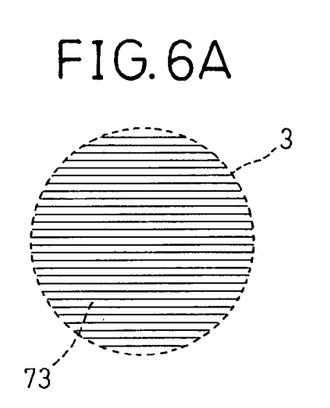
FIG. 6A is a diagram showing a first example of a pattern formed on the semiconductor wafer.
Figure 6B:
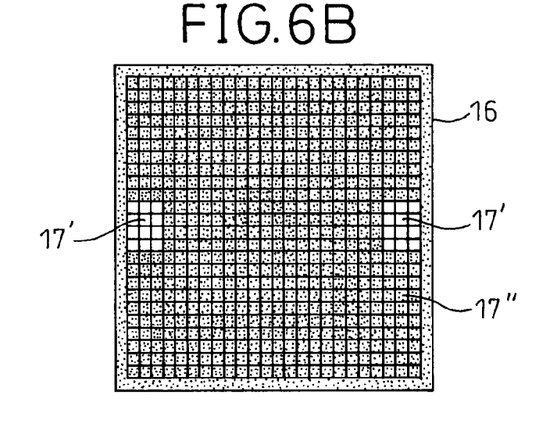
FIG. 6B is a diagram showing how the mirror array device in the illumination optical system is controlled in accordance with the pattern of FIG. 6A.
Figure 6C:
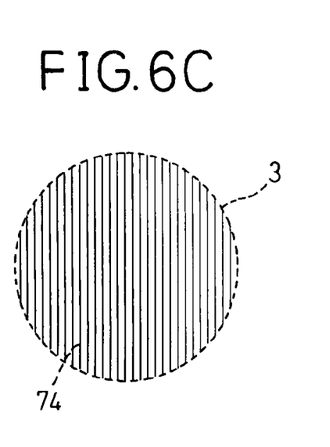
FIG. 6C is a diagram showing a second example of a pattern formed on the semiconductor wafer.
Figure 6D:
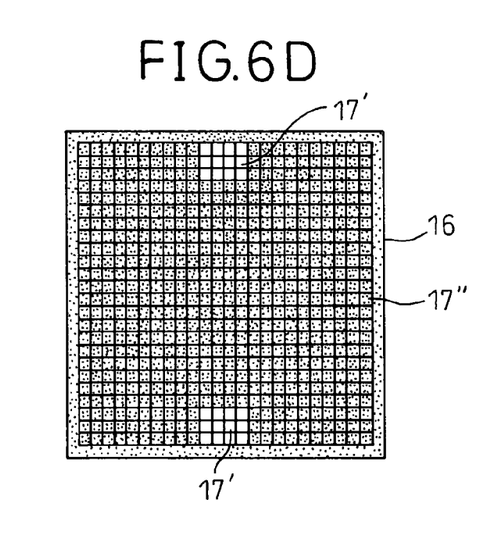
FIG. 6D is a diagram showing how the mirror array device in the illumination optical system is controlled in accordance with the pattern of FIG. 6C.

In this case, when the field of view of the objective lens 3 is located in a pattern area having an orientation with an azimuth angle (0°), such as the area 73 shown in FIG. 6A, the reflecting surfaces of the micromirrors 17 on the mirror array device 16 are controlled, for example, as shown in FIG. 6B so that the azimuth angle of the illumination light coincides with the azimuth angle of the pattern; on the other hand, when the field of view is located in a pattern area having an orientation with an azimuth angle (90°), such as the area 74 shown in FIG. 6C, the reflecting surfaces of the micromirrors 17 on the mirror array device 16 are changed, for example, as shown in FIG. 6D so that the azimuth angle of the illumination light coincides with the azimuth angle of the pattern. In this way, the mirror array device 16 is controlled so that the illumination light is always projected so as to match the direction of each pattern within the area 72; this serves to suppress the generation of scattering light from the edges of the pattern lines and enhance the sensitivity for detecting scattering light occurring from defective portions that may exist between lines. At this time, the micromirrors 27 on the mirror array device 26 in the imaging optical system may be controlled as described with reference to FIG. 4B, thus achieving a dark-field illumination system.

In FIGS. 6B and 6D, the mirrors 17" located in the hatched area are the micromirrors whose orientation is controlled so as not to reflect the light toward the lens 13, and the other mirrors 17' outside the hatched area are the micromirrors whose orientation is controlled so as to reflect the light toward the lens 13.

To change the shape of the illumination light as well as the shape of the spatial filter in accordance with the pattern of each area on the surface of the sample 2 located within the field of view of the objective lens 3, the appearance inspection apparatus of the present embodiment may comprise: a calculator 61 which can be implemented by a computer or the like; an input/output unit 63 for inputting pattern data indicating the kind of pattern formed in each area on the semiconductor wafer 2; a storage unit 64 for storing the pattern data input from the input/output unit 63; and a mirror controller 65 which, based on the position information of the stage 1 supplied from the stage controller 66, reads out of the pattern data stored in the storage unit 64 the kind of the pattern formed in the designated area on the semiconductor wafer 2 placed on the stage 1, and which individually controls the micromirrors 17 and 27 on the mirror array devices 16 and 26 in accordance with the kind of the pattern thus readout.

As the position of the semiconductor wafer 2 placed on the stage 1 is known, the mirror controller 65, based on the position information of the stage 1 supplied from the stage controller 66, can detect in which area, on the semiconductor wafer 2 placed on the stage 1, is located the field of view of the objective lens 3. The mirror controller 65 thus reads out of the pattern data stored in the storage unit 64 the kind of the pattern formed in the detected area on the semiconductor wafer 2, and controls the micromirrors 17 and 27 on the mirror array devices 16 and 26 in accordance with the kind of the pattern thus readout.

The information concerning the kind of the pattern formed in each area on the semiconductor wafer 2, which is contained in the pattern data, may be information concerning the orientation of the pattern in that area, as earlier described.

Alternatively, the information may be one for simply identifying whether the area is a memory cell area or a logic circuit area or peripheral area. In this case, when the field of view of the objective lens 3 is, for example, located in a memory cell area, dark-field illumination may be achieved by the mirror controller 65 controlling the mirror array device 16 as shown in FIG. 4A, while controlling the mirror array device 26 so as to form a spatial filter as will be described hereinafter.

On the other hand, when the field of view of the objective lens 3 is located in a logic circuit area or a peripheral area, bright-field illumination may be achieved by controlling the mirror array devices 16 and 26 so that they simply work as plane mirrors.

As described above, by controlling the mirror array device 16, the mirror controller 65 can change the shape of the image of the illumination light, to be formed in the pupil plane 8 of the objective lens 3, dynamically and as desired while scanning the objective lens 3 for inspection; at the same time, by controlling the mirror array device 26, the shape of the spatial filter for blocking or transmitting the desired portion of the projected image of the sample projected at the pupil plane 8 of the objective lens 3 can be changed dynamically and as desired while scanning the objective lens 3 for inspection.

Accordingly, when observing a designated area on the sample through the objective lens 3, the illumination light and the spatial filter that match the pattern of the designated area can be achieved, and when the field of view of the objective lens 3 enters another area as the objective lens 3 is scanned, the illumination light and the spatial filter can be changed instantaneously and dynamically to achieve illumination light and a spatial filter that match the pattern of the new area. One example of this method will be described with reference to FIG. 7 and FIGS. 8A to 8F.

Figure 7:
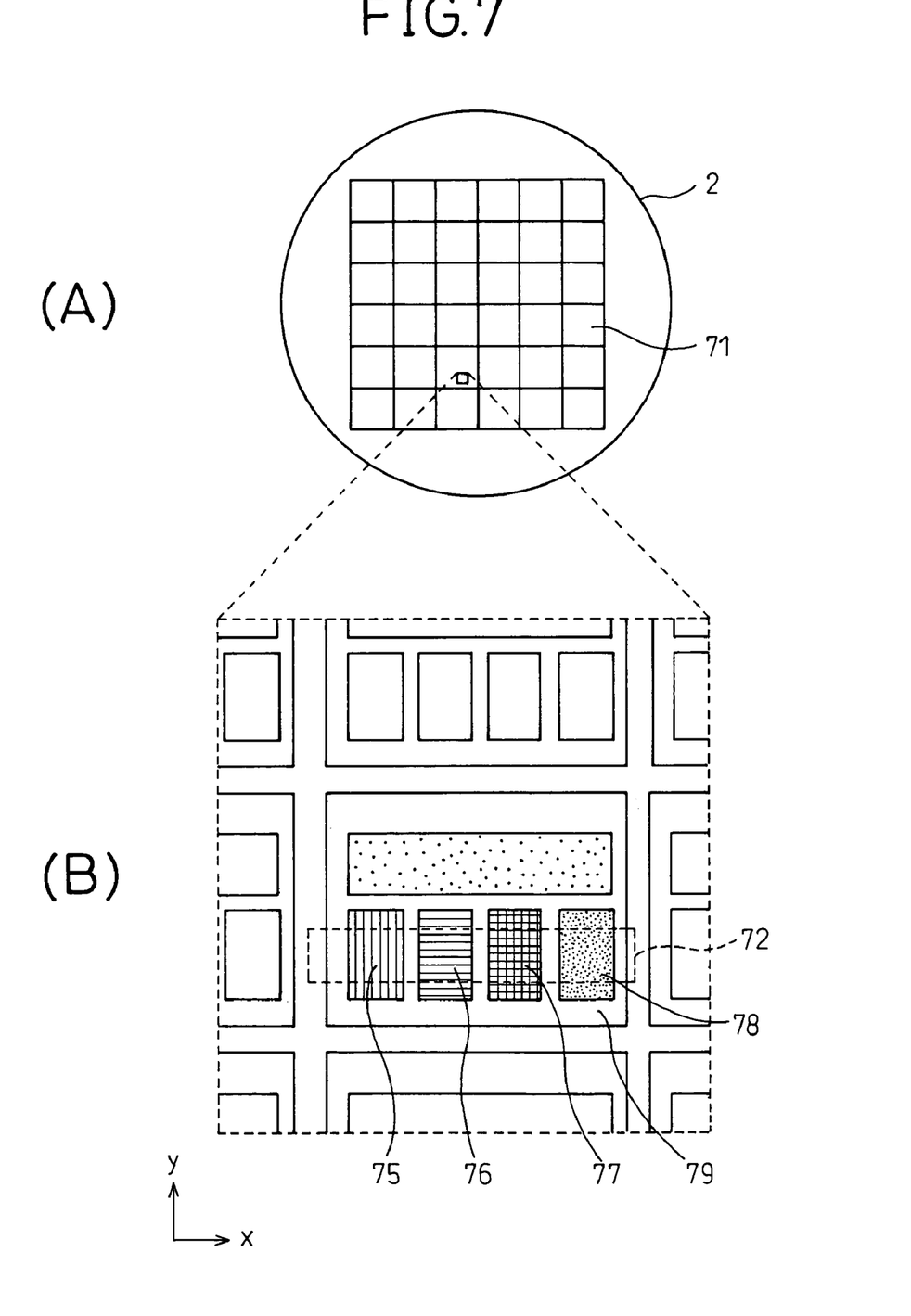

The case where various pattern areas 75 to 78 such as shown in part (B) of FIG. 7 are formed on each die 71 fabricated on the semiconductor wafer 2 as shown in part (A) of FIG. 7, and where the field of view of the objective lens 3 is scanned within the area 72 will be discussed. For example, the area 75 is a memory cell area that has a repetitive pattern repeating in periodic fashion in the x direction in the figure, the area 76 has a repetitive pattern repeating in periodic fashion in the y direction in the figure, the area 77 has a repetitive pattern repeating in periodic fashion in both the x and y directions in the figure, and the area 78 is a logic circuit area that does not have any periodic pattern. These areas 75 to 78 are surrounded by a peripheral area 79 that does not have any periodic pattern.

Figure 8A:
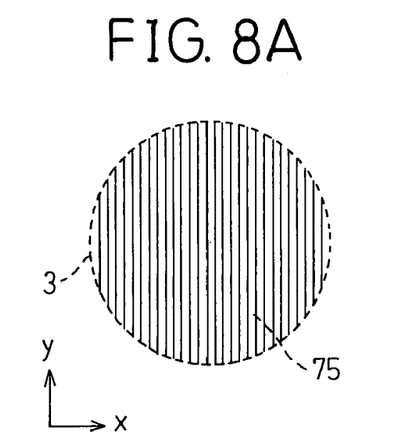
FIG. 8A is a diagram showing a third example of a pattern formed on the semiconductor wafer.
Figure 8B:
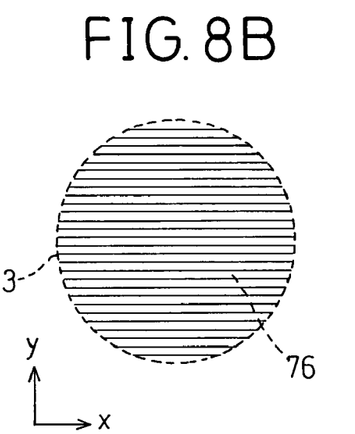
FIG. 8B is a diagram showing a fourth example of a pattern formed on the semiconductor wafer.
Figure 8C:
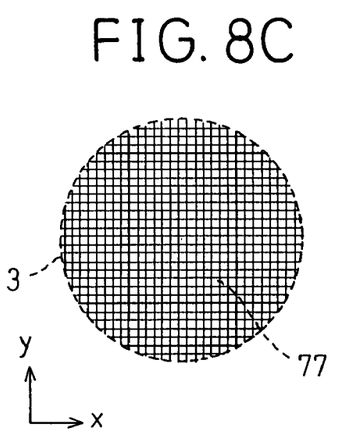
FIG. 8C is a diagram showing a fifth example of a pattern formed on the semiconductor wafer.
Figure 8D:
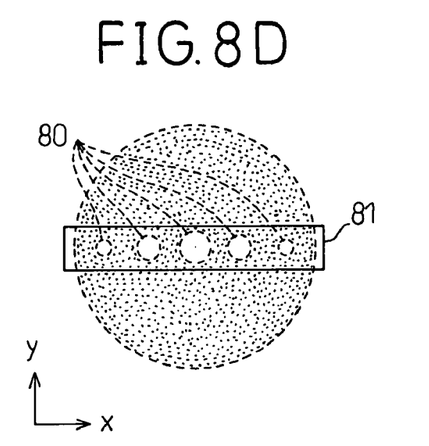
FIG. 8D is a diagram showing an Fourier transform image formed in the pupil plane of an objective lens corresponding to the pattern shown in FIG. 8A.
Figure 8E:
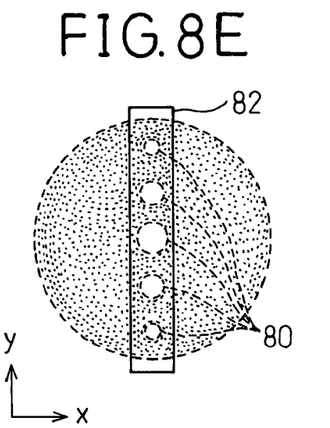
FIG. 8E is a diagram showing an Fourier transform image formed in the pupil plane of the objective lens corresponding to the pattern shown in FIG. 8B.
Figure 8F:
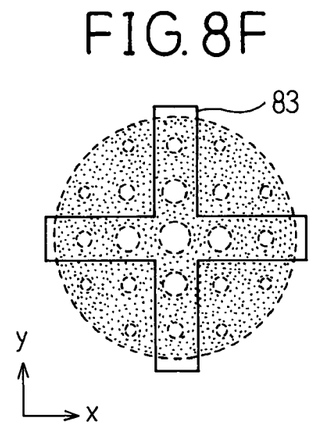
FIG. 8F is a diagram showing an Fourier transform image formed in the pupil plane of the objective lens corresponding to the pattern shown in FIG. 8C.

FIGS. 8A to 8C are diagrams showing the pattern areas 75 to 77 each captured within the field of view of the objective lens 3, and FIGS. 8D to 8F are diagrams showing the Fourier transform images, formed in the pupil plane 8, of the respective patterns when the respective pattern areas 75 to 77 are captured within the field of view of the objective lens 3. As previously described, an image of the frequency component intensity distribution of the pattern image captured within the field of view of the objective lens 3 is formed in the pupil plane 8 of the objective lens 3. For example, in the frequency component intensity distribution images shown in FIGS. 8D to 8F, spots 80 indicated as illuminating spots in FIGS. 8D to 8F appear as the Fourier transform images of the respective patterns in corresponding relationship to the spatial frequencies that the respective patterns of FIGS. 8A to 8C have.

Accordingly, when the mirror array device 26 placed at a point conjugate to the pupil plane 8 is controlled so as to work as a spatial filter that cuts off the areas 81 to 83 containing such spots 80 from the projected image projected on the reflecting surface of the mirror array device 26 (more specifically, the orientation of the mirrors 27 located in the positions corresponding to the respective areas 81 to 83 is controlled so as not to reflect the light toward the lens 22, and the orientation of the other mirrors 27 is controlled so as to reflect the light toward the lens 22), then the frequency components of the respective patterns 75 to 77 can be masked and the relative signal strength of diffracted light occurring from other portions, i.e., defective (short circuited) portions, can be increased.

In order to use the mirror array device 26 as a spatial filter as described above, the pattern information contained in the pattern data may include information concerning the periodicity, such as spatial frequencies and repeating direction, of each pattern area formed on the semiconductor wafer 2 under inspection. When scanning the surface of the semiconductor wafer 2 with the objective lens 3 for inspection, the mirror controller 65, based on the position information of the stage 1 supplied from the stage controller 66, detects in which area on the semiconductor wafer 2 placed on the stage 1 is located the field of view of the objective lens 3. Then, the mirror controller 65 reads out of the pattern data stored in the storage unit 64 the periodicity information of the periodic pattern formed in the detected area on the semiconductor wafer 2 and, in accordance with the periodicity information thus readout, controls the mirror array device 26 so as to work as a spatial filter that matches the periodicity of the pattern captured within the field of view of the objective lens 3.

Next, a description will be given of how the mirror array devices 16 and 26 are controlled by the mirror controller 65 when the area 72 shown in part (B) of FIG. 7 is scanned in the x direction with the field of view of the objective lens 3.

When the field of view of the objective lens 3 is located in the peripheral area 79 before the memory cell area 75, the mirror controller 65 controls all the micromirrors 17 on the mirror array device 16 so as to reflect the light toward the lens 13 so that the mirror array device 16 simply works as a plane mirror, and likewise controls all the micromirrors 27 on the mirror array device 26 in the imaging optical system so as to reflect the light toward the lens 22 so that the mirror array device 26 simply works as a plane mirror, thus providing the bright-field illumination system.

At this time, to reduce the brightness difference relative to the dark-field observation images of the memory cell areas 75 to 77 to be described later, the brightness of the illumination may be reduced by varying, in the mirror array device 16 of the illumination optical system, the ratio between the micromirrors 17', whose orientation is controlled so as to reflect the light toward the lens 13, and the micromirrors 17", whose orientation is controlled so as not to reflect the light toward the lens 13.

For example, to reduce the brightness of the illumination, the mirror controller 65 may control the mirror array device 16 as shown in FIG. 4A by reducing the proportion of the micromirrors 17' and providing doughnut-shaped illumination light; conversely, to reduce the brightness of the illumination, only the micromirrors 17' near the center of the reflective surface of the mirror array device 16 may be controlled so as to reflect the light toward the lens 13, thereby reducing the proportion of the micromirrors 17'.

Alternatively, to reduce the brightness of the illumination, the proportion of the micromirrors 17', whose orientation is controlled so as to reflect the light toward the lens 13, may be reduced by selecting micromirrors 17 at prescribed intervals (that is, one micromirror for every prescribed number of micromirrors 17) from among the micromirrors 17 arranged on the mirror array device 16, and by controlling the orientation of the plurality of selected micromirrors 17 so as not to reflect the light toward the lens 13.

Then, when the field of view of the objective lens 3 enters the memory cell area 75 as it moves in the x direction, the mirror controller 65 instantaneously changes the angles of the micromirrors 17 on the mirror array device 16 to control it as shown in FIG. 4A; at the same time, the angles of the micromirrors 27 on the mirror array device 26 are changed instantaneously to form a spatial filter for blocking the area 81 shown in FIG. 8D, thus providing dark-field illumination.

When the field of view of the objective lens 3 has reentered the peripheral area 79, the mirror controller 65 controls the mirror array devices 16 and 26 to provide bright-field illumination in the same manner as earlier described, and when the field of view of the objective lens 3 has moved into the memory cell area 75 or 76, the mirror controller 65 changes the angles of the micromirrors 17 on the mirror array device 16 to control it as shown in FIG. 4A in the same manner as described above, while also changing the angles of the micromirrors 27 on the mirror array device 26 to form a spatial filter for blocking the area 82 or 83 shown in FIG. 8E or 8F, respectively, thus providing dark-field illumination.

After that, when the field of view of the objective lens 3 has passed through the peripheral area 79 and moved into the logic circuit area 78 whose pattern, like the pattern of the peripheral area 79, does not have any periodicity, the mirror controller 65 maintains the mirror array devices 16 and 26 in the same conditions as when the field of view of the objective lens 3 is located in the peripheral area 79, and thus provides bright-field illumination as described above.

With the mirror controller 65 controlling the mirror array devices 16 and 26 as described above, the illumination light and the spatial filter can be changed instantaneously and dynamically in accordance with the pattern within the field of view of the objective lens 3 that changes as the objective lens 3 is scanned across the area under inspection.

According to the present invention, by configuring the illumination optical system as a reflecting optical system with a mirror array device disposed at a point conjugate to the pupil position of the objective lens, the shape of the illumination light to be focused at the pupil position of the objective lens can be changed dynamically and as desired during inspection. As a result, when performing an appearance inspection, a method of illumination that matches the pattern on the sample located within the field of view of the objective lens and the illumination light that matches the pattern can be provided, and this serves to enhance the sensitivity for defect detection.

Furthermore, according to the present invention, by configuring the imaging optical system as a reflecting optical system with a mirror array device disposed at a point conjugate to the pupil position of the objective lens, the spatial filter (spatial frequency filter) for the projection of the image of the sample can be changed dynamically during observation.

For example, when the observation area is located in a periodic pattern area such as a memory cell area, dark-field illumination can be achieved by controlling the mirror array device in the illumination optical system so that doughnut-shaped illumination light formed by blocking its center portion containing the optical axis of the objective lens is projected to the objective lens, while also controlling the mirror array device in the imaging optical system so as to form, at the conjugate point 23 to the pupil plane 8 of the objective lens, a spatial filter that cuts off the frequency component signals; on the other hand, when the observation area has moved into a logic circuit area or other peripheral circuit area (peripheral area), bright-field illumination can be provided by controlling the mirror array device in the illumination optical system and/or the imaging optical system so that the mirror array device simply works as a plane mirror. In this way, when the observation area is located in a periodic pattern area, dark-field observation can be performed, in which the signal strength of the imaging signal of the pattern itself is reduced and thereby the relative signal strength of the diffracted light occurring from a defective portion is increased, and when the observation area has moved into a logic circuit area or the like, the illumination can be dynamically switched so as to perform bright-field observation.

While the invention has been described with reference to specific embodiments chosen for purpose of illustration, it should be apparent that numerous modifications could be made thereto, by those skilled in the art, without departing from the basic concept and scope of the invention.

What is claimed is:

1. An appearance inspection apparatus comprising:
  a light source;
  an objective lens;
  an illumination optical system for projecting illumination light from said light source onto a sample through said objective lens; and
  an imaging optical system for projecting an image of said sample, projected through said objective lens, onto an imaging device, wherein
  said illumination optical system is configured as a reflecting optical system with a first mirror array device disposed at a point conjugate to a pupil position of said objective lens, and
  said imaging optical system is configured as a reflecting optical system with a second mirror array device disposed at a Fourier transformation plane in said imaging optical system.

2. An appearance inspection apparatus as claimed in claim 1, further comprising mirror controller for controlling said first mirror array device in accordance with a field-of-view position of said objective lens on said sample.

3. An appearance inspection apparatus as claimed in claim 1, further comprising mirror controller for controlling said second mirror array device in accordance with the field-of-view position of said objective lens on said sample.

4. A method of image projection in an appearance inspection apparatus, the method comprising:
  projecting illumination light from a light source onto a sample through an objective lens;
  projecting an image of said sample, projected through said objective lens, onto an imaging device;
  disposing a first mirror array device at a point conjugate to a pupil position of said objective lens;
  filtering said illumination light from said light source through said first mirror array device;
  disposing a second mirror array device at a Fourier transformation plane in an imaging optical system; and
  filtering the image of said sample projected through said objective lens through said second mirror array device.

5. A method of image projection as claimed in claim 4, further comprising controlling said first mirror array device in accordance with a field-of-view position of said objective lens on said sample.

6. A method of image projection as claimed in claim 4, further comprising controlling said second mirror array device in accordance with the field-of-view position of said objective lens on said sample.

* * * * *